United States Patent [19]

Förster et al.

[11] 4,194,054
[45] Mar. 18, 1980

[54] PREPARATION OF SUBSTITUTED FLUOROBENZENES

[75] Inventors: Heinz Förster, Wuppertal; Hans Klusacek, Cologne; Arthur Wenz, Leverkusen, all of Fed. Rep. of Germany

[73] Assignee: Bayer Aktiengesellschaft, Leverkusen, Fed. Rep. of Germany

[21] Appl. No.: 849,294

[22] Filed: Nov. 7, 1977

[30] Foreign Application Priority Data

Nov. 20, 1976 [DE] Fed. Rep. of Germany ....... 2652810

[51] Int. Cl.² ..................... C07C 25/04; C07C 25/13; C07C 63/12
[52] U.S. Cl. .......................... 562/493; 260/558 P; 260/578; 260/646; 260/650 F; 568/639; 568/645; 568/647; 568/656
[58] Field of Search .......... 260/650 F, 612 R, 612 D, 260/578, 558 P, 613 R, 575 A; 568/656, 639, 647; 562/493

[56] References Cited

U.S. PATENT DOCUMENTS

| | | | |
|---|---|---|---|
| 3,160,623 | 12/1964 | Anello et al. | 260/505 R |
| 3,950,444 | 4/1976 | Gay | 260/650 F |

FOREIGN PATENT DOCUMENTS 600706  3/1933  Fed. Rep. of Germany .

OTHER PUBLICATIONS

Wallach, Annalen der Chemie, 235 pp. 233-271 (1886).
Fieser et al., Reagents for Organic Synthesis, vol. I, pp. 445-446 (1967).
Aldrech Catalog Handbook of Fine Chemicals, p. 483 (1978).

Primary Examiner—Jane S. Myers
Attorney, Agent, or Firm—Sprung, Felfe, Horn, Lynch & Kramer

[57] ABSTRACT

A process for the preparation of a substituted fluorobenzene of the formula

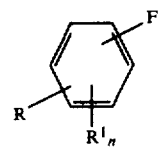

in which
R is alkyl, alkoxy, halogen, amino, acylamido, carboxyl, benzyloxy, aryloxy, or benzyloxy or aryloxy carrying at least one alkyl, alkoxy, halogen or halogenoalkyl substituent,
$R^1$ each independently is alkyl or halogen, and
n is an integer from 0 to 4, comprising reacting an N-aryl-N',N'-dialkyl-triazene of the formula

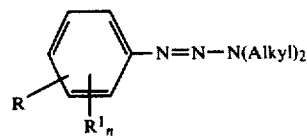

in which
Alkyl is alkyl with 1 to 4 carbon atoms, with about a 5 to 25-fold molar excess of anhydrous hydrofluoric acid at a temperature between about −20° and +150° C.

10 Claims, No Drawings

PREPARATION OF SUBSTITUTED FLUOROBENZENES

A process for the preparation of a substituted fluorobenzene of the formula

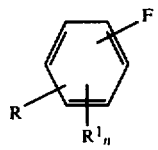

in which

R is alkyl, alkoxy, halogen, amino, acylamido, carboxyl, benzyloxy, aryloxy, or benzyloxy or aryloxy carrying at least one alkyl, alkoxy, halogen or halogenoalkyl substituent, $R^1$ each independently is alkyl or halogen, and n is an integer from 0 to 4, comprising reacting an N-aryl-N',N'-dialkyl-triazene of the formula

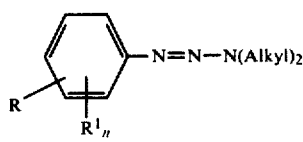

in which

Alkyl is alkyl with 1 to 4 carbon atoms, with about a 5 to 25-fold molar excess of anhydrous hydrofluoric acid at a temperature between about −20° and +150° C.

The present invention relates to an unobvious process for the preparation of certain aromatic fluorine compounds (some of which are known) which can be used as intermediates for the synthesis, for example, of insecticidal and acaricidal active compounds and/or pharmaceuticals.

It is already known that certain aromatic fluorine compounds containing fluorine bonded to the nucleus may be prepared industrially from aromatic amines by diazotization, for example with sodium nitrite in anhydrous hydrofluoric acid at 5° C., and subsequent warming of the diazonium fluoride solution (see German Reichspatent No. 600,706).

However, this process has the disadvantage that 2 moles of water of reaction are formed per mole of fluoroaromatic compound formed, which can lead to increased formation of phenolic impurities, whereby the yield falls and the purity does not correspond to the demands made. A large excess of hydrofluoric acid must be used in this process in order to suppress the formation of the undesired phenols. The excess hydrofluoric acid can only be recovered in the anhydrous form with a high expenditure of time and money.

Furthermore, it is known that aromatic fluorides are obtained when N-aryl-triazenes are reacted with aqueous concentrated hydrofluoric acid [see O. Wallach, Annalen der Chemie 235 (1886) page 255-271]. For example, phenyldiazopiperidide has been reacted with concentrated aqueous hydrofluoric acid and, after warming the mixture, fluorobenzene and piperidinium fluoride have been obtained, with the elimination of nitrogen. However, this process also has the disadvantages already mentioned above for the process carried out industrially, that is to say poor yields and impurities, in particular phenols, in the process products. Moreover, corrosion problems arise when working with aqueous concentrated hydrofluoric acid, which latter disadvantage is absolutely avoided by the present process.

There is thus great interest in a process which has none of these deficiencies and which gives the products not only in good yields but also in high purity.

The present invention provides a process for the production of an aromatic fluorine compound of the general formula

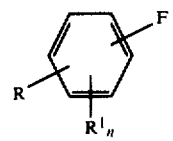 (I).

in which

R represents alkyl, alkoxy, halogen, amino, acylamido, carboxyl, benzyloxy or aryloxy, the benzyl or aryl radical of the two last-mentioned groups optionally carrying one or more substituents selected independently from alkyl, alkoxy, halogen and halogenoalkyl, $R^1$ represents alkyl or halogen and n represents zero or an integer from 1 to 4, the $R^1$ substituents being selected independently when n is 2 or more, in which an N-aryl-N',N'-dialkyl-triazene of the general formula

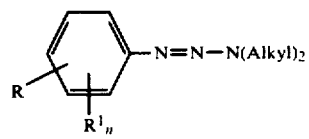 (II).

in which

R, $R^1$ and n have the meanings stated above, and

Alkyl represents alkyl with 1 to 4 carbon atoms, preferably methyl, is reacted with anhydrous hydrofluoric acid, using about a 5 to 25-fold molar excess of the latter, at temperatures between about −20° and 150° C., optionally in the presence of a solvent and optionally under nitrogen, under normal pressure or under increased pressure.

Preferably, R represents straight-chain or branched alkyl with 1 to 6 (especially 1 to 3) carbon atoms, straight-chain or branched alkoxy with 1 to 4 (especially 1 to 3) carbon atoms, fluorine, chlorine, bromine, amino, acetamido, propionamido, butyrylamido, carboxyl, benzyloxy or phenyloxy, the phenyl radical of the two last-mentioned groups optionally carrying one or more substituents selected independently from fluorine, chlorine, trifluoromethyl and straight-chain or branched alkyl with 1 to 4 carbon atoms (especially methyl or ethyl) and $R^1$ represents straight-chain or branched alkyl with 1 to 4 carbon atoms (especially methyl or ethyl) or chlorine.

The desired end products of the structure (I), which could hitherto only be prepared in poor yields and an impure form by the processes indicated above, may be obtained in very good yields and high purity in the process according to the invention. Although two reaction stages must be carried out in the process according to the invention, compared with the known processes, the additional expenditure is considered to be negligible compared with the advantages. In the procedure according to the invention, the step in which water is formed—the diazotization—is separated from the reaction in hydrofluoric acid. The reaction with hydrofluoric acid can therefore be carried out in a homogeneous, liquid phase. The corrosion problems are avoided by carrying out the process in an anhydrous medium and, in addition, the formation of phenols is suppressed. The excess hydrofluoric acid can be recovered in the anhydrous form by simple distillation and can be fed again to the reaction. Last but not least, the broad applicability of the process should be emphasized.

If N',N'-dimethyl-N-(2-methyl-phenyl)-triazene and anhydrous hydrofluoric acid are used as the starting materials, the course of the reaction can be represented by the following equation:

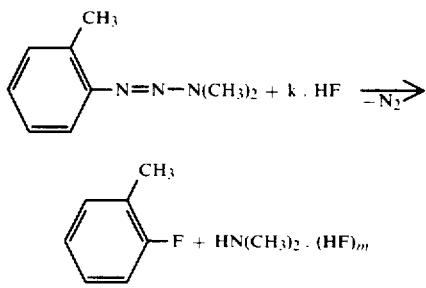

wherein k is 2 or a higher integer, and m is 1 or 2.

The N-aryl-N',N'-dialkyl-triazenes (II) to be used as starting materials can be prepared in accordance with processes which are known from the literature, by diazotizing aromatic amines, for example with sodium nitrite, and reacting the aryldiazonium salts formed with dialkylamines in an aqueous solution.

Examples which may be mentioned are: N-[3-methoxy-, 4-methoxy-, 3-ethoxy-, 4-ethoxy-, 3-methyl-, 4-methyl-, 3-ethyl-, 4-ethyl-, 4-acetylamido-, 4-propionamido-, 4-butyrylamido-, 2-carboxy-, 3-carboxy-, 4-carboxy-, 2-chloro-, 2-bromo-, 2-fluoro-, 2-amino-, 3-nitro-, 4-nitro-, 4-chloro-2-methyl-, 4-chloro-2-ethyl-, 4-bromo-2-methyl-, 4-bromo-2-ethyl-, 2,4-dimethyl-, 2,4-diethyl-, 2,6-dimethyl-, 2,6-diethyl-, 2,6-dichloro-, 2,6-dibromo-, 2-fluoro-6-methyl- or 3-benzyloxyphenyl]- and N-[3-(2,6-dichloro-4-trifluoromethylphenoxy)-phenyl]-, N-[4-(3-methylphenoxy)-phenyl]- and N-[3-(2,6-dichloro-4-trifluoromethylphenoxy)-6-methylphenyl]-N',N'-dimethyl-triazene.

The anhydrous hydrofluoric acid which is also to be used as a starting material is available as a technical product analyzing more than about 93% HF by weight.

The process according to the invention can be carried out using a suitable solvent or diluent, especially pyridine and dimethylsulphoxide. However, the process is preferably carried out without using a solvent or diluent.

The diazonium fluorides formed from the N-aryl-N',N'-dialkyltriazenes (II) during the reaction with anhydrous hydrofluoric acid are split to give the fluorine compounds of the formula (I). This splitting is carried out between about −20° and +150° C., preferably between about −10° and +110° C., and particularly advantageously between about 0° and 80° C.

If the temperatures used are above the boiling point of hydrogen fluoride (about 20° C.), the reaction is generally carried out under the autogenous pressure of the hydrogen fluoride, that is to say under increased pressure, and without a solvent. These reaction conditions are the most advantageous.

However, it is also possible to carry out the reaction under normal pressure and in the presence of a solvent or diluent.

To carry out a preferred embodiment of the process according to the invention, the triazene component and the anhydrous hydrofluoric acid are mixed at −10° to 0° C., in particular by initially introducing a 10-20-fold molar excess of anhydrous hydrofluoric acid and adding the triazene component, while cooling. The reaction is now carried out by heating the mixture to the reaction temperature in an autoclave or by passing the mixture through a reaction zone which is preheated to the reaction temperature.

In general, the subsequent working-up is carried out by distilling off the excess hydrofluoric acid and distilling the reaction mixture. In order to separate off the dialkylamine hydrofluoride, the distillate can also be washed with water, or the reaction mixture is added to water, the aqueous phase is extracted by shaking with an organic solvent, for example methylene chloride, and the organic phase is worked up in the customary manner by washing, drying and distillation.

The process products are usually colorless to pale yellow-colored liquids which can be identified and characterized by their refractive index, their boiling point or by gas chromatography.

As already mentioned above, the aromatic fluorine compounds which can be prepared according to the process may be used, for example, as intermediates for the syntheses of insecticidal active compounds and/or pharmaceuticals (see, for example, German Offenlegungsschrift No. (German Published Specification) 2,547,534).

The preparative examples which follow illustrate the process according to the invention.

EXAMPLE 1:

(a)

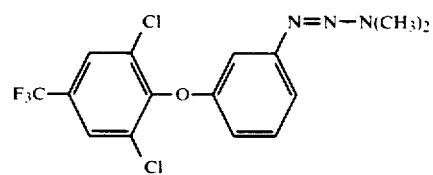

107 g (0.3 mol) of 2,6-dichloro-4-trifluoromethyl-3'-amino-diphenyl ether hydrochloride were dissolved in 400 ml of water and 30 ml of concentrated hydrochloric acid were added. A solution of 20.7 g (0.3 mol) of sodium nitrite in 100 ml of water was added dropwise to this mixture at 0° C., while cooling. The mixture was subsequently stirred for one hour. This solution was then allowed to run gradually into a mixture of 39.2 g (0.35 mol) of 40% strength dimethylamine solution, 60 g of sodium carbonate, 210 ml of water and 300 ml of chloroform at 0° C., while cooling. The mixture was stirred for at least 2 hours at room temperature. The phases were then separated and the organic phase was washed with water, dried over sodium sulphate and concentrated. 99 g (88% of theory) of N-[3-(2,6- dichloro-4-trifluoromethylphenoxy)-phenyl]-N',N'-dimethyltriazene remained in the form of yellow-brown crystals with a melting point of 123° C.

(b)

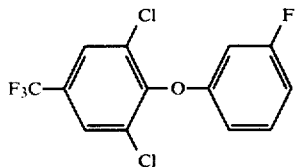
(1)

300 ml of anhydrous hydrofluoric acid were initially introduced into a 2 liter stirred autoclave and 140 g (0.37 mol) of the compound prepared under (a) were added at −5° to 0° C. The autoclave was closed, nitrogen was introduced until its pressure reached 3 bars and it was heated slowly.

| Time (minutes) | Temperature (°C.) | Pressure (bars) |
|---|---|---|
| 0 | 24 | 3 |
| 28 | 50 | 3.75 |
| 35 | 78 | 5.5 released to 5.2 |
| 36 | 78 | 5.9 released to 5.2 |
| 37 | 78 | 5.7 released to 5.2 |
| 39 | 80 | 5.7 released to 5.2 |
| 54 | 80 | 5.35 |
| 79 | 80 | 5.35 |

The autoclave was then cooled, the pressure was released and the mixture was transferred into a distillation apparatus of stainless steel. The excess hydrofluoric acid was distilled off up to a bath temperature of 100° C. (248 g), and the mixture was then distilled in vacuo. A colorless two-phase distillate passed over uniformly at 132°–135° C./3–5 mm Hg (120 g); residue 18.5 g. The distillate was taken up in methylene chloride and the methylene chloride solution was washed with water, dried over sodium sulphate and concentrated (101 g). The concentrate was subjected to fractional distillation in vacuo and 95 g (80% of theory) of, according to the gas chromatogram, 99.6% pure 2,6-dichloro-4-trifluoromethyl-3'-fluoro-diphenyl ether were obtained with a boiling point of 109°–111° C./0.08 mm Hg.

EXAMPLE 2:

126 g of N-[4-(3-fluorophenoxy)-2-methylphenyl]-N',N'-dimethyl-triazene were added dropwise to 200 ml of 100% strength hydrofluoric acid at −5° to 0° C. and the reaction mixture was then heated to 100° C. in an autoclave. It was left for 1 hour at 100° C., the pressure rising to 12.3 atmospheres. After cooling, the 154 g of the dark-colored two-phase residue were taken up in methylene chloride and the organic phase was washed with water, dried and concentrated. The 96 g of substance were distilled in vacuo and 75 g (74% of theory) of 3-fluoro-4'-fluoro-3'-methyldiphenyl ether were thus obtained with a boiling point of 114° C./0.25 mm Hg.

EXAMPLE 3:

400 ml (20 mol) of anhydrous hydrofluoric acid were cooled to about −30° C. in a 3-liter autoclave and 485 g (1.9 mol) of N-[4-(3-methyl-phenoxy)-phenyl]-N',N'-dimethyltriazene were then added in the course of 30 minutes, while stirring and further cooling. The mixture was then heated slowly to about 100° C. in the sealed autoclave.

| Time (minutes) | Temperature (°C.) | Pressure (bars) |
|---|---|---|
| 0 | 20 | 0 |
| 30 | 45 | 0 |
| 60 | 55 | 0 |
| 90 | 75 | 0 |
| 120 | 90 | 5 |
| 150 | 100 | 12 |
| 180 | 100 | 25 |
| 210 | 100 | 29 |
| 240 | 100 | 31 |
| 270 | 100 | 34 |

The autoclave was cooled (20° C., 19 bars) and the mixture was poured onto about 5 kg of ice and extracted with methylene chloride. The methylene chloride extracts were dried and concentrated. 362 g of a dark oil remained, which was subjected to fractional distillation. 260 g (68% of theory) of 4-fluoro-3'-methyl-diphenyl ether with a boiling point of 94°–97° C./0.14 mm Hg and 43 g of a black, resinous residue were obtained.

The compounds shown in the following table were obtained by methods analogous to those of the above examples:

| Ex. No. | Triazenes of the formula Z—N=N—N(CH$_3$)$_2$ Z | Aryl fluoride (end product) | Reaction temperature °C.; boiling point °C. | Yield (% of theory) |
|---|---|---|---|---|
| 4 | H$_3$C—⌬— | H$_3$C—⌬—F | 50–60; 112 | 68 |
| 5 | H$_3$C—⌬(CH$_3$)— | H$_3$C—⌬(CH$_3$)—F | 45–50; 143–144 | 70 |

| Ex. No. | Triazenes of the formula Z—N=N—N(CH₃)₂ Z | Aryl fluoride (end product) | Reaction temperature °C.; boiling point °C. | Yield (% of theory) |
|---|---|---|---|---|
| 6 | CH₃–C₆H₄– | CH₃–C₆H₄–F | 85–95; 114–115 | 59 |
| 7 | Cl–C₆H₃(CH₃)– | Cl–C₆H₃(CH₃)–F | 80–85; 47 | 63 |
| 8 | H₃CO–C₆H₄– | H₃CO–C₆H₄–F | 100; 155 | 56 |
| 9 | H₃CO–C₆H₄– | H₃CO–C₆H₄–F | 25–30; 153–154 | 54 |
| 10 | F₃C–C₆H₂(Cl)₂–O–C₆H₃(CH₃)– | F₃C–C₆H₂(Cl)₂–O–C₆H₃(CH₃)–F | 25–30; 117–119/0.45 mm Hg | 88 |
| 11 | C₆H₄(CH₃)–CO–OH | C₆H₃(F)(CO–OH)– | 70–80; 114 | 64 |
| 12 | NO₂–C₆H₄– | NO₂–C₆H₃–F | 80–90; 82–83/15 mm Hg | 60 |
| 13 | C₆H₅–O–C₆H₃(CH₃)– | C₆H₅–O–C₆H₃(CH₃)–F | 80–100; 83–84/0.1 mm Hg | 65 |
| 14 | H₃C–C₆H₃(Br)– | H₃C–C₆H₂(Br)(F)– | 115–120; 72–74/14 mm Hg | 83 |

It will be appreciated that the instant specification and examples are set forth by way of illustration and not limitation, and that various modifications and changes may be made without departing from the spirit and scope of the present invention.

What is claimed is:

1. A process for the preparation of a substituted fluorobenzene of the formula

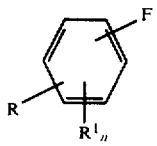

in which

R is alkyl with 1 to 6 carbon atoms, alkoxy with 1 to 4 carbon atoms, fluorine, chlorine, bromine, amino, acetamido, propionamido, butyrylamido, carboxyl, benzyloxy, phenyloxy, benzyloxy or phenyloxy carrying at least one fluorine, chlorine, trifluoromethyl or alkyl substituent with 1 to 4 carbon atoms, and R¹ is alkyl with 1 to 4 carbon atoms or chlorine, and n is an integer from 0 to 4, comprising reacting an N-aryl-N',N'-dialkyl-triazene of the formula

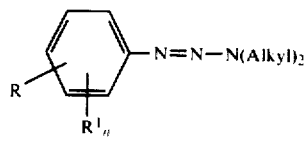

in which

Alkyl is alkyl with 1 to 4 carbon atoms, with about a 5 to 25-fold molar excess of anhydrous hydrofluoric acid at a temperature between about −20° and +150° C.

2. A process according to claim 1, in which the reaction is effected under nitrogen.

3. A process according to claim 1, in which the reaction is carried out without a solvent.

4. A process according to claim 3, in which the reaction is effected under elevated pressure at a temperature above about 20° C.

5. A process according to claim 1, in which the reaction is effected in the presence of a diluent or solvent.

6. A process according to claim 5, in which the solvent or diluent is dimethylsulphoxide or pyridine.

7. A process according to claim 1, in which the reaction is effected at between about −10° and +110° C.

8. A process according to claim 1, in which the triazene is added to about a 10–20-fold molar excess of anhydrous hydrogen fluoride.

9. A process according to claim 1, in which each Alkyl is methyl.

10. A process according to claim 1, in which each Alkyl is methyl, the triazene is added to about a 10–20-fold molar excess of anhydrous hydrogen fluoride, and the reaction is effected between about 20° and 80° C.

* * * * *